United States Patent
Wang et al.

(10) Patent No.: US 12,235,178 B2
(45) Date of Patent: Feb. 25, 2025

(54) SQUATTING BIONIC DEVICE OF HUMAN LOWER-LIMB JOINT

(71) Applicant: HENAN POLYTECHNIC UNIVERSITY, Jiaozuo (CN)

(72) Inventors: Jianping Wang, Jiaozuo (CN); Yanqing Wang, Jiaozuo (CN); Shaokai Sun, Jiaozuo (CN); Xu Chen, Jiaozuo (CN); Jinlai Liu, Jiaozuo (CN); Junqi Yue, Jiaozuo (CN)

(73) Assignee: HENAN POLYTECHNIC UNIVERSITY, Jiaozuo (CN)

( * ) Notice: Subject to any disclaimer, the term of this patent is extended or adjusted under 35 U.S.C. 154(b) by 245 days.

(21) Appl. No.: 17/927,698

(22) PCT Filed: Jan. 21, 2021

(86) PCT No.: PCT/CN2021/073153
§ 371 (c)(1),
(2) Date: Nov. 24, 2022

(87) PCT Pub. No.: WO2021/253827
PCT Pub. Date: Dec. 23, 2021

(65) Prior Publication Data
US 2023/0213400 A1    Jul. 6, 2023

(30) Foreign Application Priority Data

Jun. 15, 2020  (CN) .......................... 202010544225.9

(51) Int. Cl.
*G01L 5/1627*    (2020.01)
(52) U.S. Cl.
CPC .................. *G01L 5/1627* (2020.01)
(58) Field of Classification Search
CPC ...... G01L 5/1627; A61F 2/4657; A61F 2/468; A61F 2002/4666; A61F 2/4684;
(Continued)

(56) References Cited

U.S. PATENT DOCUMENTS

| 4,235,025 A | 11/1980 | Kortge |
| 5,014,719 A * | 5/1991 | McLeod ............ A61B 5/4528 |
| | | 600/595 |

FOREIGN PATENT DOCUMENTS

| CN | 105266932 A | 1/2016 |
| CN | 204971715 U | 1/2016 |

(Continued)

OTHER PUBLICATIONS

Adrija Sharma, et al., In vivo patellofemoral forces in high flexion total knee arthroplasty, Journal of Biomechanics, 2008, pp. 642-648, vol. 41.

(Continued)

*Primary Examiner* — John Fitzgerald
*Assistant Examiner* — Truong D Phan
(74) *Attorney, Agent, or Firm* — Bayramoglu Law Offices LLC

(57) ABSTRACT

A squatting bionic device of a human lower-limb joint is provided. In the squatting bionic device, a vertical support plate is provided on the device with a sliding table, which is driven by a first motor to slide up and down in a height direction of the vertical support plate or to be fixed on the vertical support plate. A horizontal fixed shaft is fixed on the sliding table. The middle of the fixed shaft is connected with a femoral shaft through a first universal joint. A lower end of the femoral shaft is fixedly connected with a lower femur simulation block. A wire rope is wound around a rotation shaft of a second motor fixed on a base. One end of the wire rope is fixed on the rotation shaft of the second motor, and the other end thereof extends upwards.

10 Claims, 13 Drawing Sheets

(58) Field of Classification Search
CPC ...... A61F 2002/4667; A61F 2002/7635; A61F 2002/7645; A61B 5/11; A61B 5/1038; A61B 8/485; A61B 2562/0261
See application file for complete search history.

(56) References Cited

FOREIGN PATENT DOCUMENTS

| | | |
|---|---|---|
| CN | 106510907 A | 3/2017 |
| CN | 107328574 A | 11/2017 |
| CN | 108542559 A | 9/2018 |
| CN | 108766169 A | 11/2018 |
| CN | 208140287 U | 11/2018 |
| CN | 209312318 U | 8/2019 |
| CN | 209751299 U | 12/2019 |
| CN | 111568613 A | 8/2020 |

OTHER PUBLICATIONS

K.E. Moglo, et al., Cruciate coupling and screw-home mechanism in passive knee joint during extension-flexion, Journal of Biomechanics, 2005, pp. 1075-1083, vol. 38.

Azhar M. Merican, et al., Iliotibial band tension affects patellofemoral and tibiofemoral kinematics, Journal of Biomechanics, 2009, pp. 1539-1546, vol. 42.

* cited by examiner

SQUATTING BIONIC DEVICE OF HUMAN LOWER-LIMB JOINT

CROSS REFERENCE TO THE RELATED APPLICATIONS

This application is the national phase entry of International Application No. PCT/CN2021/073153, filed on Jan. 21, 2021, which is based upon and claims priority to Chinese Patent Application No. 202010544225.9, filed on Jun. 15, 2020, the entire contents of which are incorporated herein by reference.

TECHNICAL FIELD

The present invention relates to the field of biomechanics, in particular to a squatting bionic device of a human lower-limb joint.

BACKGROUND

The structural design of hip, knee and ankle joints is the most critical component in the design of a human lower limb device. The hip joint is a ball-and-socket joint, and its center of rotation does not change significantly during rotation. The ankle joint is a compound joint, but its rotation angle is small during walking, so the change in the center of rotation is not obvious. These two exoskeleton joints can be simplified into single joints that rotate around a fixed axis. The knee joint is also a compound joint. Additionally, the knee joint is the largest and most complex joint in the human body. It plays an especially important role in the body's weight-bearing and movement. The knee joint is composed of patella, distal femur, proximal tibia and upper tibia. The stability of the knee joint is closely related to its biomechanical properties. At present, a series of physical examination tests, such as anterior drawer test, Lachman test, and others, are typically used clinically to test the biomechanical properties of the knee joint, so as to evaluate its stability. There has been no biomechanical test instrument for the knee joint for a long time. Doctors rely on their hands to apply torque to the knee joint and feel the slight displacement of the knee joint. This method is significantly influenced by subjective factors and depends heavily on the doctors' experience. It is difficult to perform quantitative comparison, and younger less experienced doctors may have difficulty effectively performing the test.

At present, current knee joint measuring instruments include the Kneela.x3, the KT1000/KT2000 and other known devices. These knee joint measuring instruments quantitatively load tension and pressure on the tibia of the knee joint and measure the distance of the tibia in anterior/posterior translation. This is in order to achieve the purpose of quantitatively testing the biomechanical properties of the knee joint. However, they can only apply the tension and pressure, not torque, to the tibia, and can only measure the displacement perpendicular to the tibia. Knee joint displacement is a compound movement, including translations and rotations such as medial/lateral rotation and adduction/abduction, all of which cannot be accurately measured by the current knee joint measuring instrument. In 1951, the first generation of a hinged artificial knee joint was designed. The improved joint achieved uniaxial flexion and extension of 110°, and it used acrylic as the prosthesis material. By the 1960s, a fully constrained knee joint fixed with bone cement began to be used, while the material was developed from the original stainless steel transitioning to cobalt-based alloy. By the 1970s, a semi-constrained artificial knee joint began use. While the stability of the fully constrained artificial knee joint was maintained, the semi-constrained artificial knee joint had a larger range of movement. Since then, the metal/ultra-high molecular weight polyethylene joint combination has been further developed by using a "rolling in groove" design. Chinese patent 201611058599.X discloses a device for testing and evaluating a biomechanical property of a knee joint. The patented device includes a frame module, a joint fixation module, a knee joint module, a joint flexion drive module and a loading module. The device simulates a movement state of a human lower-limb joint by adjusting a flexion angle of the knee joint, and tests a stress state of an interface between a bionic bone tissue and a prosthesis under different flexion angles of the knee joint by loading an external force. The device is limited by volume and configuration, however, and can only be used to measure stress distribution at the interface between the bionic bone tissue and the prosthesis. Chinese patent 201520657904.1 discloses an artificial knee-joint bionic mechanism. The bionic mechanism includes a femur rod, a femoral component, a meniscus and a tibia rod. The bionic mechanism can realize the rotation, flexion, extension, rolling and sliding functions of the human knee joint, but because it does not take into account the hip joint and ankle joint, it cannot effectively simulate the flexion movement of the human lower limb. It is necessary to improve people's understanding of knee biomechanics, especially orthopedic surgeons, so as to facilitate the development of surgical operations to some extents.

SUMMARY

In order to overcome the above-mentioned deficiencies of the prior art, the present invention provides a squatting bionic device of a human lower-limb joint. The present invention can effectively acquire bionic squatting forces and movement trails of a human lower limb.

The present invention has a technical solution as follows:

A squatting bionic device of a human lower-limb joint includes a support, and the support has a base and a vertical support plate vertically provided on one side of the base. The vertical support plate is provided thereon with a sliding table, which is driven by a first motor to slide up and down in a height direction of the vertical support plate or to be fixed on the vertical support plate. A horizontal fixed shaft is fixed on the sliding table. The middle of the fixed shaft is connected with a femoral shaft through a first universal joint. A lower end of the femoral shaft is fixedly connected with a lower femur simulation block.

A plantar position adjustment mechanism is provided on the base. A tibial shaft is connected with the plantar position adjustment mechanism through a second universal joint. An upper end of the tibial shaft is connected with an upper tibia simulation block.

An upper end of the upper tibia simulation block is inserted with a meniscus connection block. An upper end of the meniscus connection block is provided with a meniscus clamping slot. A meniscus simulation block is compressed and fixed in the meniscus clamping slot on a top surface of the meniscus connection block.

A lower end of the lower femur simulation block is provided with a circular arc surface in a shape corresponding to a lower end of a human femur. The circular arc surface is supported on the meniscus simulation block. Upper femoral ligament clamps are respectively fixed on both sides of the lower femur simulation block. Lower femoral ligament clamps corresponding to the upper femoral ligament clamps are respectively fixed on both sides of the upper tibia simulation block. A ligament simulation band is connected between the upper femoral ligament clamp and the lower femoral ligament clamp. A patellar ligament clamp is fixed on the front of the upper tibia simulation block. An upwardly extending patellar ligament simulation band is fixedly connected with the patellar ligament clamp.

A wire rope is wound around a rotation shaft of a second motor fixed on the base. One end of the wire rope is fixed on the rotation shaft of the second motor, and the other end thereof extends upwards, passes around a fixed pulley block fixed on the sliding table, and is connected with an upper end of the patellar ligament simulation band.

Preferably, a rail provided in a vertical direction is fixed on a side of the vertical support plate close to the center of the base. The rail is slidably provided with a sliding table fixing plate that slides up and down in a length direction of the rail. The vertical support plate is fixed with the first motor above the rail. A lead screw parallel to the length direction of the rail is rotatably provided in front of the rail. The rotation shaft of the first motor faces vertically downward and a lower end thereof is fixedly connected with an upper end of the lead screw. The lead screw is screwed with a nut fixed with the sliding table fixing plate to form a driving structure that makes the sliding table fixing plate slide up and down in the length direction of the rail. The sliding table is fixed on a side of the sliding table fixing plate away from the rail.

Preferably, the first motor is fixed directly above the lead screw by a top motor fixing plate. The rotation shaft of the first motor passes through the motor fixing plate and is coaxially connected with the upper end of the lead screw through a coupling. A slider is fixed on a side of the sliding table fixing plate close to the rail. The slider is slidably provided on the rail.

Preferably, the squatting bionic device of a human lower-limb joint further includes a controller, a tension sensor, a strain meter, a first gyroscope, a second gyroscope, a first strain gauge and a second strain gauge. The first strain gauge is provided between the top surface of the meniscus connection block and a bottom surface of the meniscus simulation block. The second strain gauge is provided between an upper surface of a bottom ankle joint sliding table and a lower surface of a top ankle joint sliding table. The tension sensor is provided on each wire rope. The first gyroscope is fixed on the femoral shaft. The second gyroscope is fixed on the tibial shaft. An output terminal of the controller is connected with the first motor and the second motor. An output terminal of the first strain gauge, an output terminal of the second strain gauge, an Output terminal of the first gyroscope, an output terminal of the second gyroscope and an output terminal of the tension sensor are respectively connected with an input terminal of the controller.

Preferably, a wire rope stranding guide sleeve is fixed on the femoral shaft. There are three second motors. The rotation shaft of each second motor is wound with a wire rope. The three wire ropes pass around the fixed pulley block, pass through the wire rope stranding guide sleeve, and are connected with the upper end of the patellar ligament simulation band.

The device of the present invention simulates the human lower limb through the femoral shaft, the meniscus simulation block, the tibial shaft and the plantar position adjustment mechanism, and simulates the squat of the lower limb by adjusting the height through the sliding table. Since the upper end of the femoral shaft and the lower end of the tibial shaft are connected by a universal joint, when the device simulates the squat of the human body, the femoral shaft and the tibial shaft simulate the movement trail of the lower limb in a three-dimensional direction. This device simulates the main muscles of the lower limb through three wire ropes, acquires the applied squatting force through the tension sensor, acquires the movement trail signal during the squat process through the gyroscope, and acquires the forces on the knee joint and the sole through the strain gauge. In this way, the device simulates the movement trail of the human lower limb under a certain force during squatting, and simulates the main bone and soft tissue structure of the human lower limb, as well as the stress state of the main muscles and ligament tissues during squatting. This device tests the biomechanical properties of the knee joint of the human body during exercise, and acquires the biomechanical properties of the knee joint of the human body at various flexion angles, so as to comprehensively measure the forces and compound movement trails (medial/lateral rotation and adduction/abduction, etc.) of the human lower limb. Meanwhile, this device acquires basic data such as the forces on the joint and sole, provides a biomechanical data basis for the exercise, rehabilitation and surgical treatment of the lower limb and joint of the human body, and also provides effective bionic data for the production of lower limb prostheses. This device is convenient to use and has desired effects. It is an innovation in the bionic device of the human lower-limb joint and achieves excellent social and economic benefits.

DETAILED DESCRIPTION OF THE EMBODIMENTS

Figure 1:
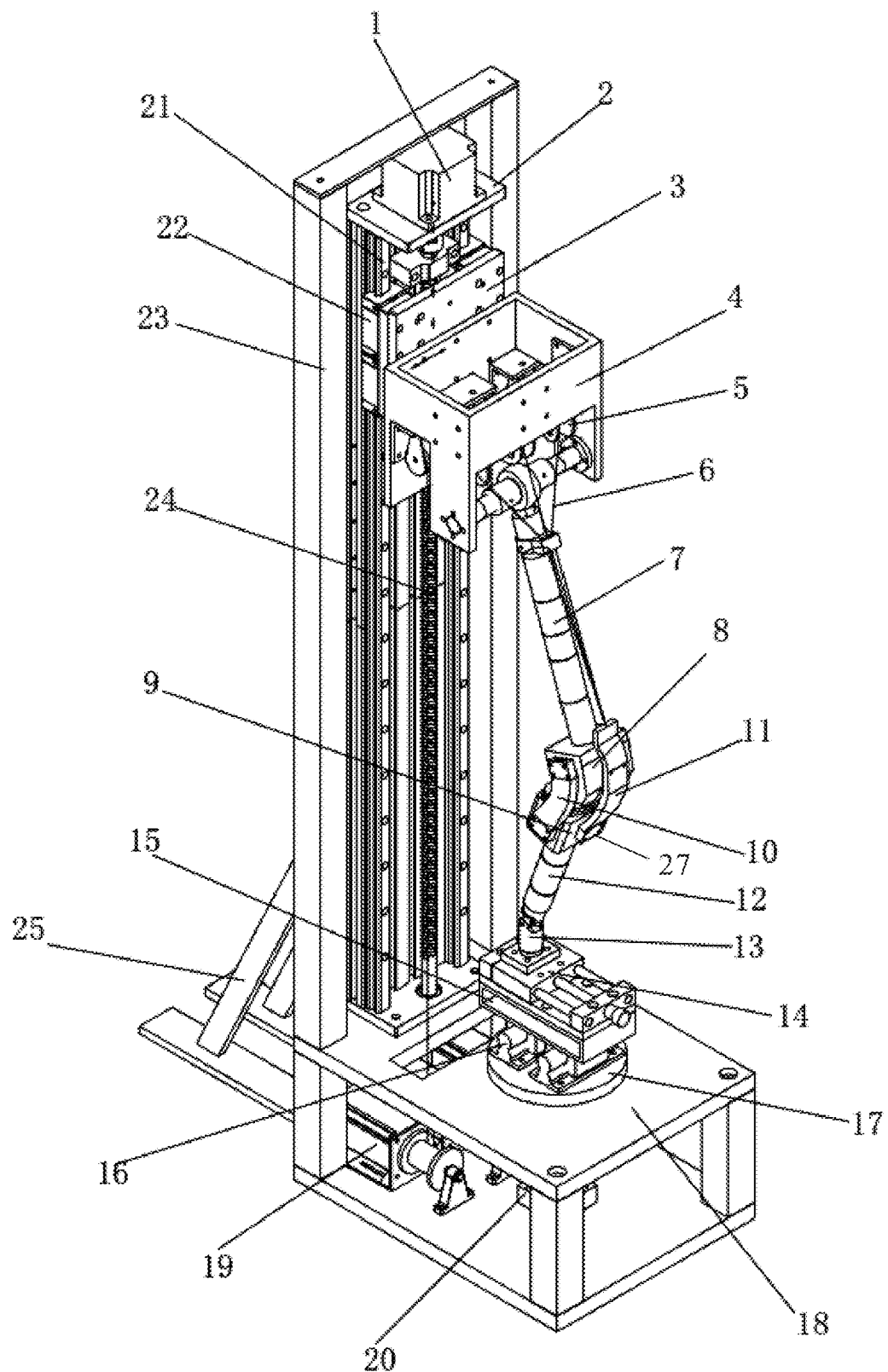
FIG. 1 is a stereoscopic view of the present invention.
Figure 2:
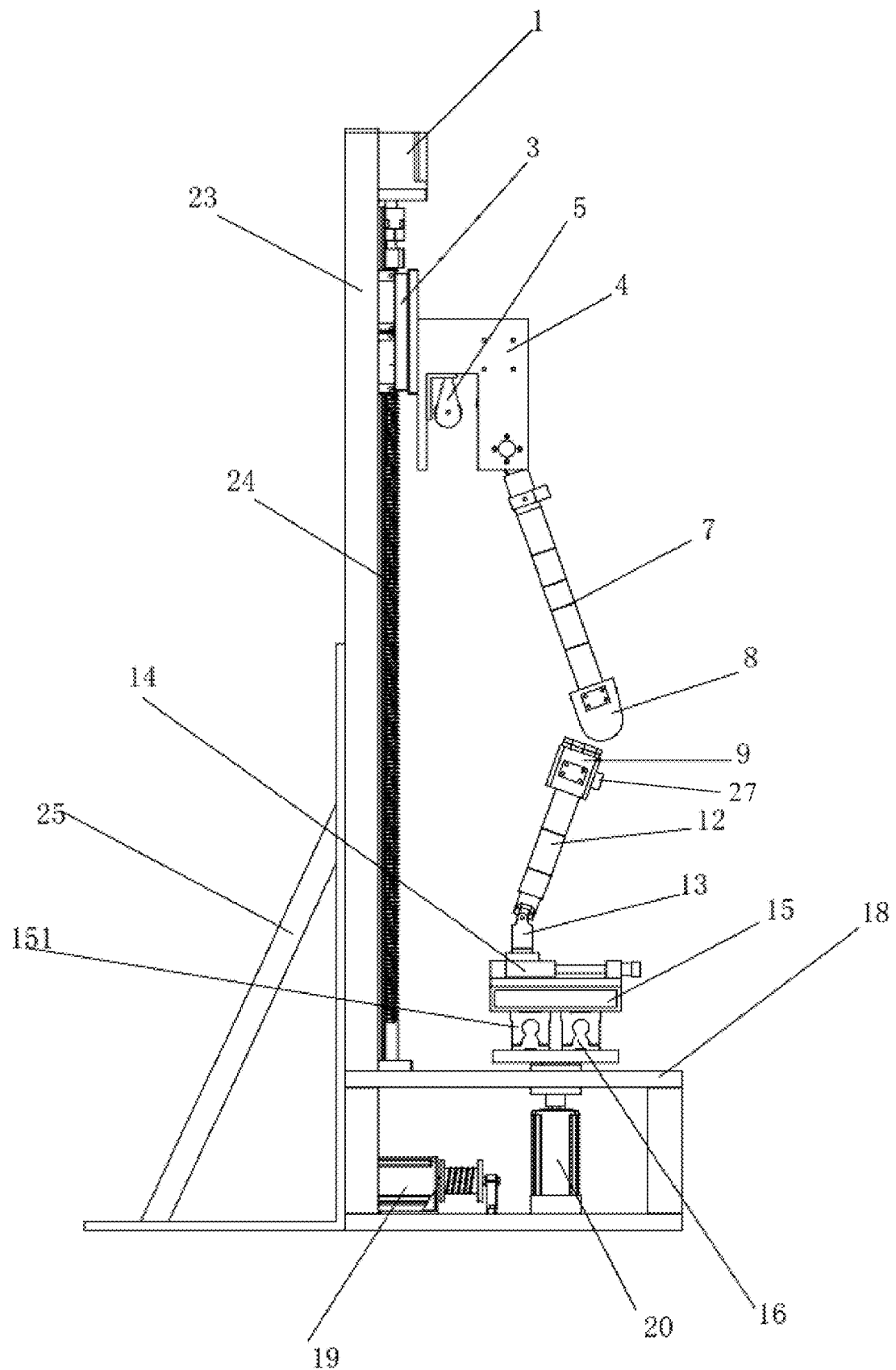
FIG. 2 is a lateral view of the present invention.
Figure 3:
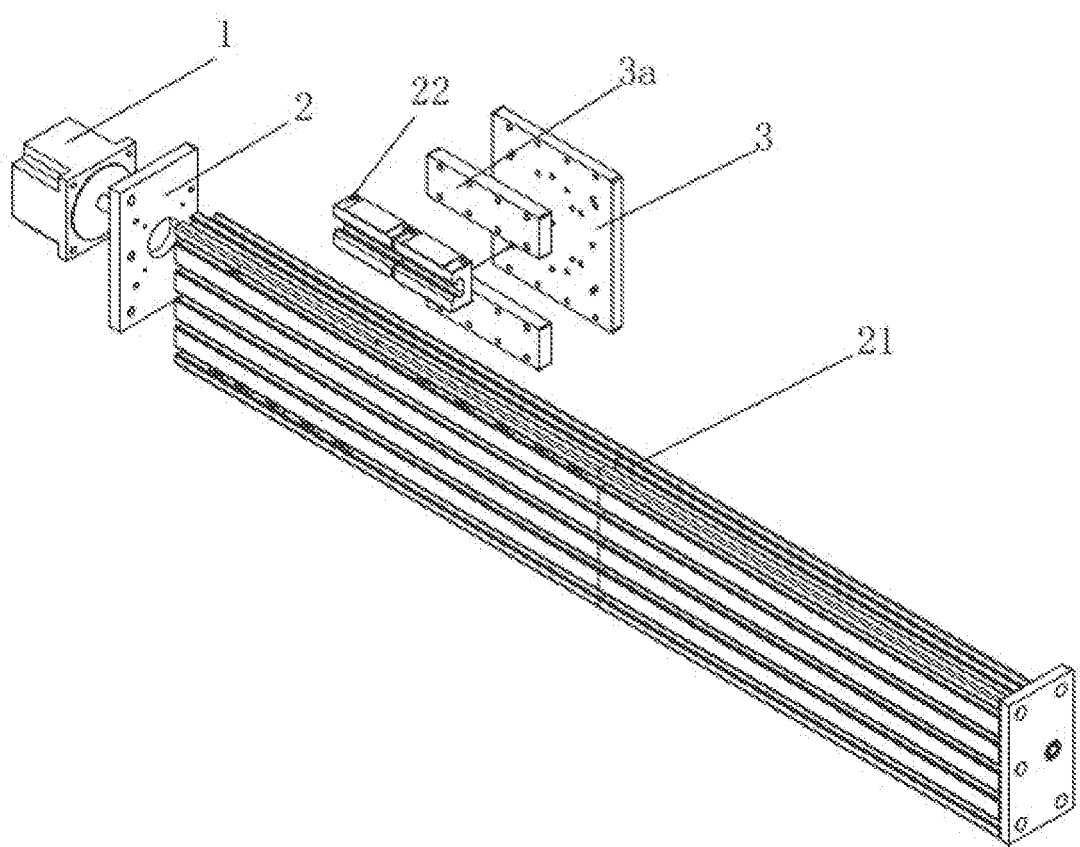
FIG. 3 is an exploded view of a rail according to the present invention.
Figure 4:
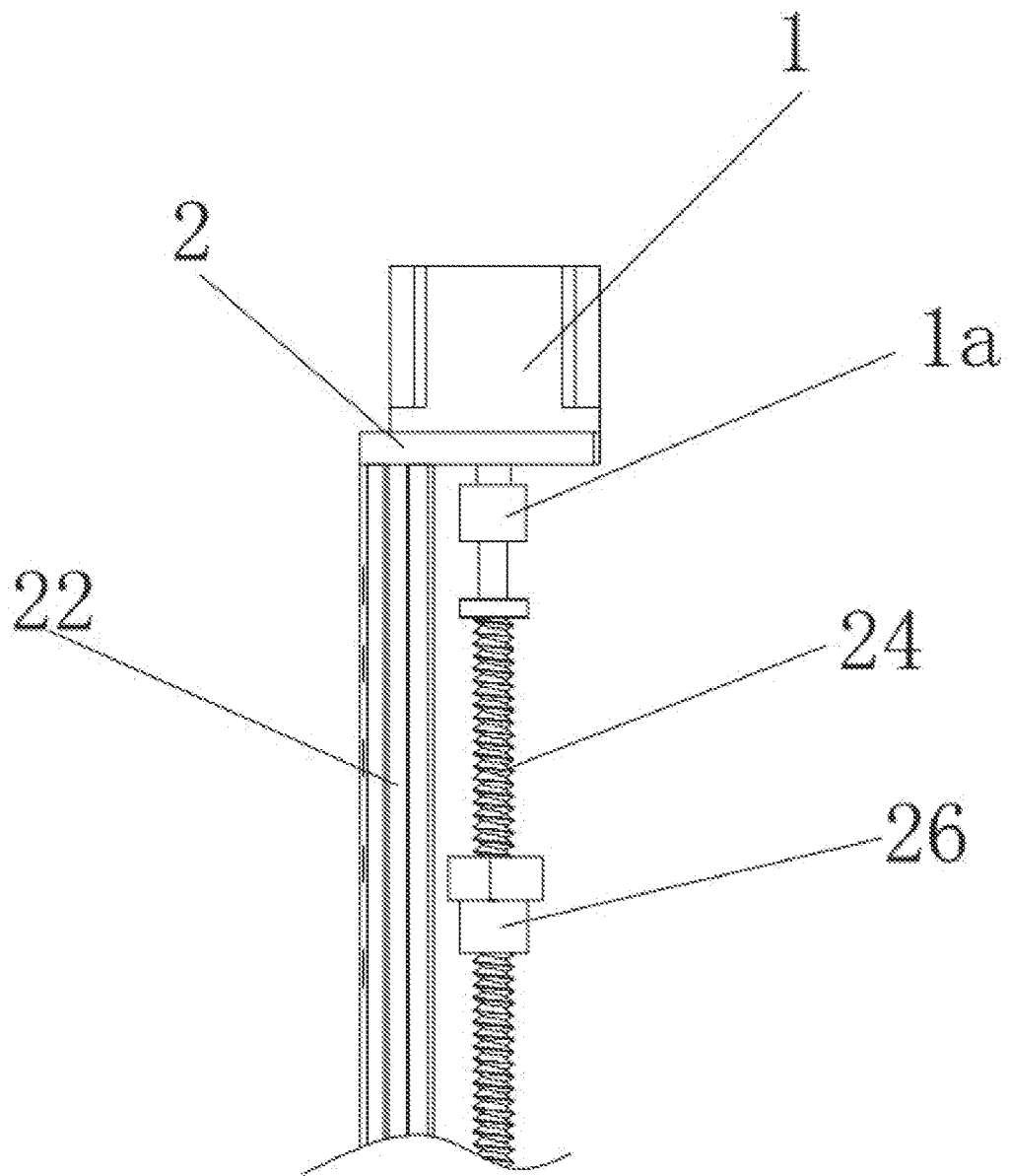
FIG. 4 is a partial enlarged view of an upper part of a lead screw according to the present invention.

The specific implementations of the present invention are described in further detail below with reference to the accompanying drawings.

The present invention provides a squatting bionic device of a human lower-limb joint. As shown in FIGS. 1-11, the squatting type bionic device includes a support. The support includes a base 18 and a vertical support plate 23 vertically provided on one side of the base 18, The vertical support plate 23 is provided thereon with a sliding table 4 which is driven by a first motor 1 to slide up and down in a height direction of the vertical support plate or to be fixed on the vertical support plate. A horizontal fixed shaft 41 is fixed on the sliding table. The middle of the fixed shaft 41 is connected with a femoral shaft 7 through a first universal joint. A lower end of the femoral shaft 7 is fixedly connected with a lower femur simulation block 8.

A plantar position adjustment mechanism is provided on the base 18. A tibial shaft 12 is connected with the plantar position adjustment mechanism through a second universal joint 13. An upper end of the tibial shaft 12 is connected with an upper tibia simulation block 9.

An upper end of the upper tibia simulation block 9 is inserted with a meniscus connection block 92. An upper end of the meniscus connection block 92 is provided with a meniscus clamping slot. A meniscus simulation block 91 is compressed and fixed in the meniscus clamping slot on a top surface of the meniscus connection block.

A lower end of the lower femur simulation block 8 is provided with a circular arc surface in a shape corresponding to a lower end of a human femur. The circular arc surface is supported on the meniscus simulation block 91. Upper femoral ligament clamps 8a are respectively fixed on both sides of the lower femur simulation block 8. Lower femoral ligament clamps 9a corresponding to the upper femoral ligament clamps are respectively fixed on both sides of the upper tibia simulation block 9. A ligament simulation band 10 is connected between the upper femoral ligament clamp 8a and the lower femoral ligament clamp 9a. A patellar ligament clamp 27 is fixed on the front of the upper tibia simulation block 9. An upwardly extending patellar ligament simulation band 11 is fixedly connected with the patellar ligament clamp 27.

A wire rope 6 is wound around a rotation shaft of a second motor 19 fixed on the base 18. One end of the wire rope 6 is fixed on the rotation shaft of the second motor, and the other end thereof extends upwards, passes around a fixed pulley block 5 fixed on the sliding table 4, and is connected with an upper end of the patellar ligament simulation band 11.

In order to ensure the effect of use, a rail 21 provided in a vertical direction is fixed on a side of the vertical support plate 23 close to the center of the base. The rail 21 is slidably provided with a sliding table fixing plate 3 that slides up and down in a length direction of the rail. The vertical support plate is fixed with the first motor 1 above the rail 21. A lead screw 24 parallel to the length direction of the rail is rotatably provided in front of the rail 21. The rotation shaft of the first motor 1 faces vertically downward and a lower end thereof is fixedly connected with an upper end of the lead screw 24. The lead screw 24 is screwed with a nut 26 fixed with the sliding table fixing plate 3 to form a driving structure that makes the sliding table fixing plate slide up and down in the length direction of the rail. The sliding table 4 is fixed on a side of the sliding table fixing plate away from the rail.

The first motor 1 is fixed directly above the lead screw by a top motor fixing plate 2. The rotation shaft of the first motor 1 passes through the motor fixing plate 2 and is coaxially connected with the upper end of the lead screw 24 through a coupling 1a. A slider 22 is fixed on a side of the sliding table fixing plate 3 close to the rail. The slider is slidably provided on the rail. The slider 22 is fixed on the sliding table fixing plate through symmetrical connecting plates 3a on both sides, and the nut 26 is fixed between the two connecting plates 3a. When in use, the first motor is started to drive the lead screw to rotate. Because the sliding table and the rail are coordinated with each other, the sliding table fixing plate can only slide up and down in the rail. Therefore, during the rotation of the lead screw, the nut is driven to rotate and slide up and down in the lead screw, thereby driving the sliding table fixing plate to slide up and down in the rail, forming a height adjustment mechanism of the sliding table.

The squatting bionic device of a human lower-limb joint further includes a controller, a tension sensor, a strain meter, a first gyroscope, a second gyroscope, a first strain gauge and a second strain gauge. The first strain gauge is provided between the top surface of the meniscus connection block 92 and a bottom surface of the meniscus simulation block 91. The second strain gauge is provided between an upper surface of a bottom ankle joint sliding table 15 and a lower surface of a top ankle joint sliding table 14. The tension sensor is provided on each wire rope. The first gyroscope is fixed on the femoral shaft 7. The second gyroscope is fixed on the tibial shaft 12. An output terminal of the controller is connected with the first motor and the second motor. An output terminal of the first strain gauge, an output terminal of the second strain gauge, an output terminal of the first gyroscope, an output terminal of the second gyroscope and an output terminal of the tension sensor are respectively connected with an input terminal of the controller.

The bottom ankle joint sliding table 15 and the top ankle joint sliding table 14 are compressed and fixed by bolts.

The controller is connected with a key, a display and a power supply, respectively. The key is used to input an instruction, the display is used to display detection data, and the power supply is used to supply power to various components.

The tension sensor is used to acquire a tensile force of each strand of wire rope.

The first strain gauge and the second strain gauge detect a force by acquiring a voltage signal. The first strain gauge is used to acquire a force on the knee joint, and the second strain gauge is used to acquire a force on a sole.

The first gyroscope and the second gyroscope are used to acquire movement trails of the femoral shaft 7 and the tibial shaft 12, respectively.

The first motor is used to control lifting of the sliding table, that is, to simulate a squat of the human lower limb, and a descending speed of the sliding table is a squatting speed.

The second motor applies a pulling force on the three wire ropes to simulate a muscle force.

The controller is used to control the rotation of the first motor and the second motor. Through the rotation of the first motor, a force is applied to the wire rope as a first input for muscle simulation, and the force is acquired and controlled in real time by the tension sensor. Through the rotation of the second motor, the lifting of the sliding table is controlled to simulate the squatting speed of the human lower limb as a second input. In the process of simulating the squat, the movement trail signal of the gyroscope and the force signal of the strain gauge are received, so as to simulate the movement trail of the lower limb under a certain force. The controller is an existing technology, such as a control chip with a model of STC15W401AS, a microcontroller unit (MCU) with a model of STC89C51, an MCU with a model of 8051 and a programmable logic controller (PLC). When mounting, the controller, the key, the display, the power supply and other components are directly fixed on the back of the vertical support plate.

The plantar position adjustment mechanism includes a third motor 20 fixed on the base 18. A rotation shaft of the third motor 20 is vertically upward. The rotation shaft of the third motor 20 is fixed with a turntable 17. The turntable 17 is fixed with a first ankle joint guide rail 16. The first ankle joint guide rail 16 is provided thereon with the bottom ankle joint sliding table 15 that slides in a length direction of the first guide rail or is fixed on the first ankle joint guide rail. An upper surface of the bottom ankle joint sliding table 15 is connected with the top ankle joint sliding table 14. The second universal joint is provided on the top ankle joint sliding table 14. The third motor is connected with the controller.

The bottom of the bottom ankle joint sliding table 15 is fixed with a first ankle joint guide slider 151 corresponding to the ankle joint guide rail. The first ankle joint guide slider 151 is slidably placed on the first ankle joint guide rail. A side of the first ankle joint guide slider 151 is provided with a lock switch for fixing a sliding position of the first ankle joint guide slider, which constitutes a sliding guide and lock structure of the bottom ankle joint sliding table.

The top ankle joint sliding table 14 includes a sliding table base 141. The sliding table base 141 is provided with a second ankle joint guide rail 142 and a guide screw 144 parallel to the second ankle joint guide rail. The second ankle joint guide rail 142 is slidably connected with a second ankle joint guide slider 143 that slides back and forth in a length direction of the second ankle joint guide rail. The second ankle joint guide slider 143 is threadedly connected with the guide screw 144. A position adjustment knob 145 is fixed on the guide screw extending from one side of the sliding table base 141. The second universal joint 13 is connected with the second ankle joint guide slider 143.

The lock switch may be a lock screw, and the first ankle joint guide slider may be compressed and fixed by tightening the lock screw. Alternatively, the lock switch may be a lock buckle 153 shown in FIG. 9, and the position of the first ankle joint guide slider may be locked by rotating the lock buckle. The lock buckle is an existing technology, such as a lock buckle used for adjusting the seat height of a shared bicycle. The rotation of the third motor drives the turntable to rotate. Through the sliding and fixed adjustment of the first ankle joint guide slider 151 and the second ankle joint guide slider 143, different initial positions and angles of the sole are adjusted.

The base 18 is divided into upper and lower layers by two parallel support plates. The second motor 19 and the third motor 20 are fixed on a lower support plate. The vertical support plate 23 is fixed on an upper fixing plate, and the upper fixing plate has a window for the wire rope to pass through.

The fixed shaft 41 is fixed between two side walls of the sliding table 4 through shaft seats 42 at both ends. Opposite clamping sleeves 451 are fixed and sleeved on both sides of the fixed shaft 41. The first universal joint is provided between the two clamping sleeves 451. The first universal joint comprises a spherical support 46 fixed between the two clamping sleeves. An upper end of the femoral shaft 7 is fixedly connected with a femoral joint extension connector 44 that is coaxial with the femoral shaft. A femoral joint bearing sleeve 43 is fixed at an upper end of the femoral joint extension connector 44. The femoral joint bearing sleeve 43 is movably sleeved on the spherical support 46 to form a universal connection structure.

A wire rope stranding guide sleeve 71 is fixed on the femoral shaft 7. There are three second motors 19. The rotation shaft of each second motor is wound with a wire rope. The three wire ropes pass around the fixed pulley block, pass through the wire rope stranding guide sleeve 71, and are connected with the upper end of the patellar ligament simulation band 11.

An oblique support 25 is provided on a side of the support to further keep the support stable.

Figure 5:
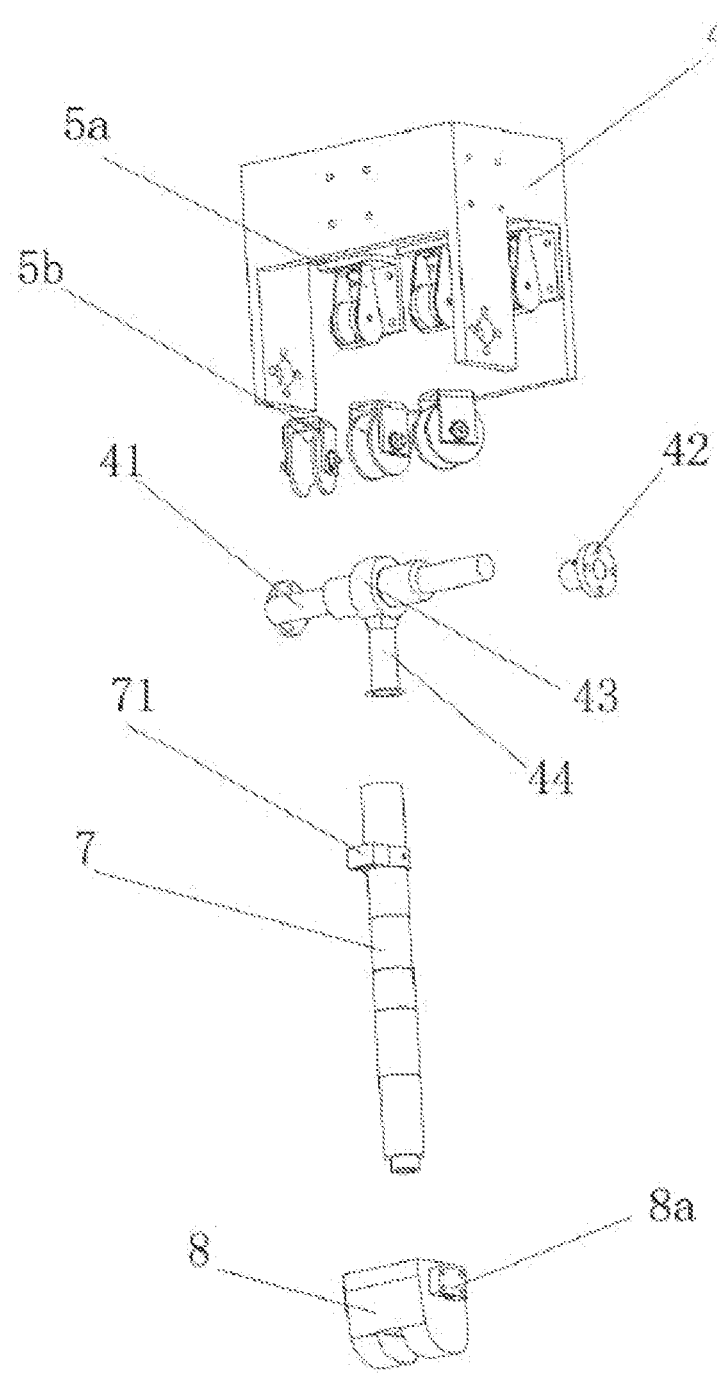
FIG. 5 an exploded view of a sliding table and a femoral shaft according to the present invention.
Figure 6:
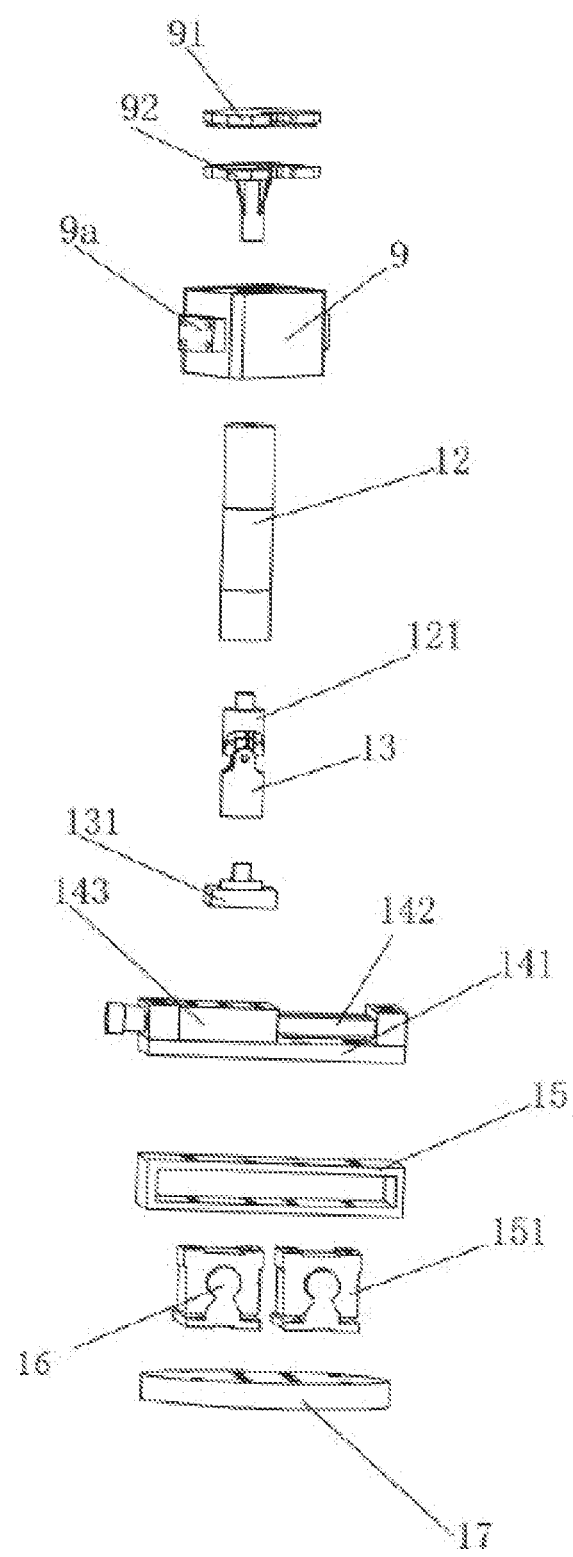
FIG. 6 is an exploded view of a tibial shaft and a bottom ankle joint sliding table according to the present invention.
Figure 7:
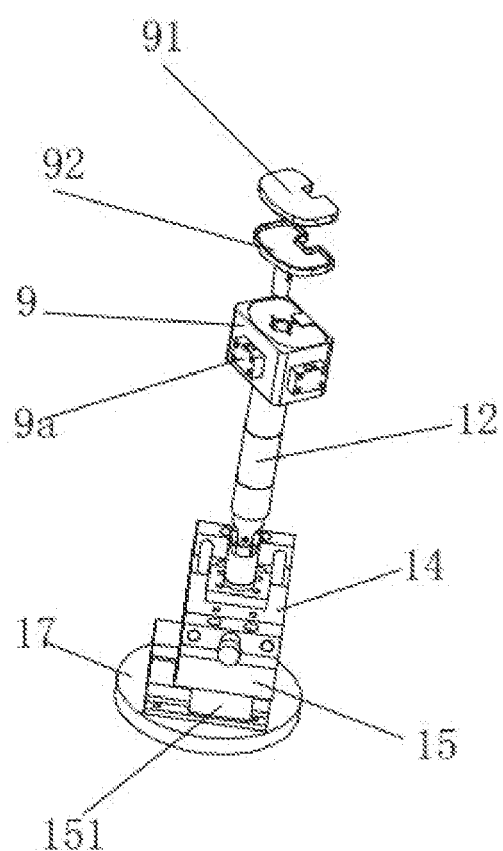
FIG. 7 is an exploded view of the tibial shaft and a meniscus simulation block according to the present invention.
Figure 8:
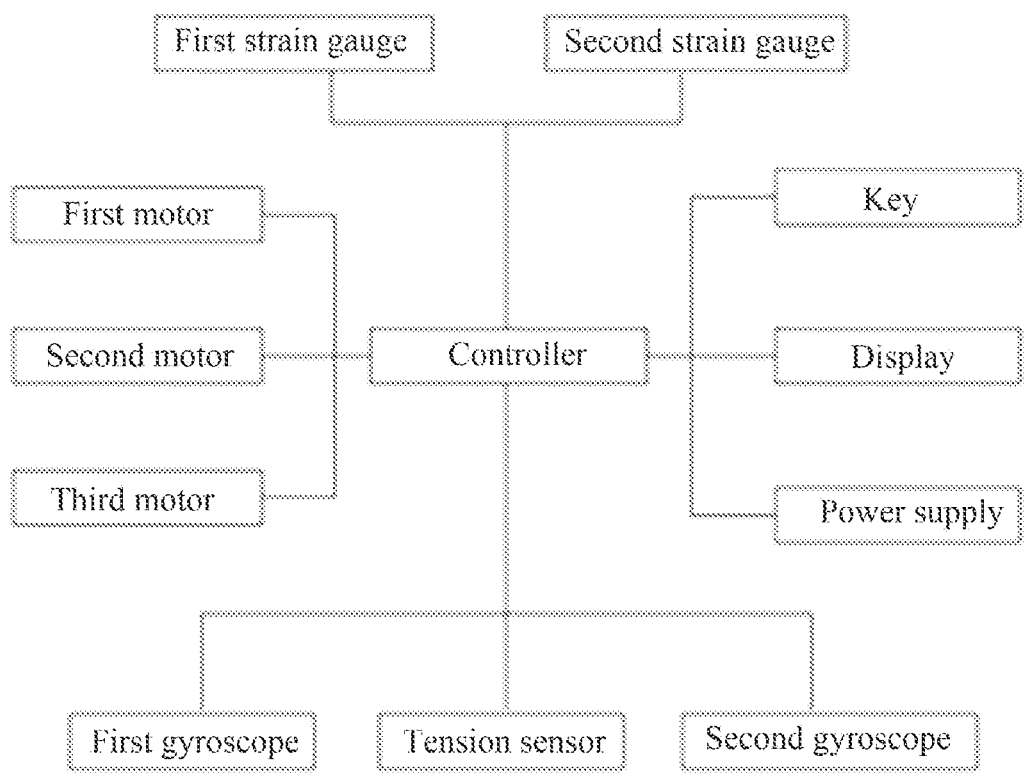
FIG. 8 is a block diagram of a circuit according to the present invention.
Figure 9:
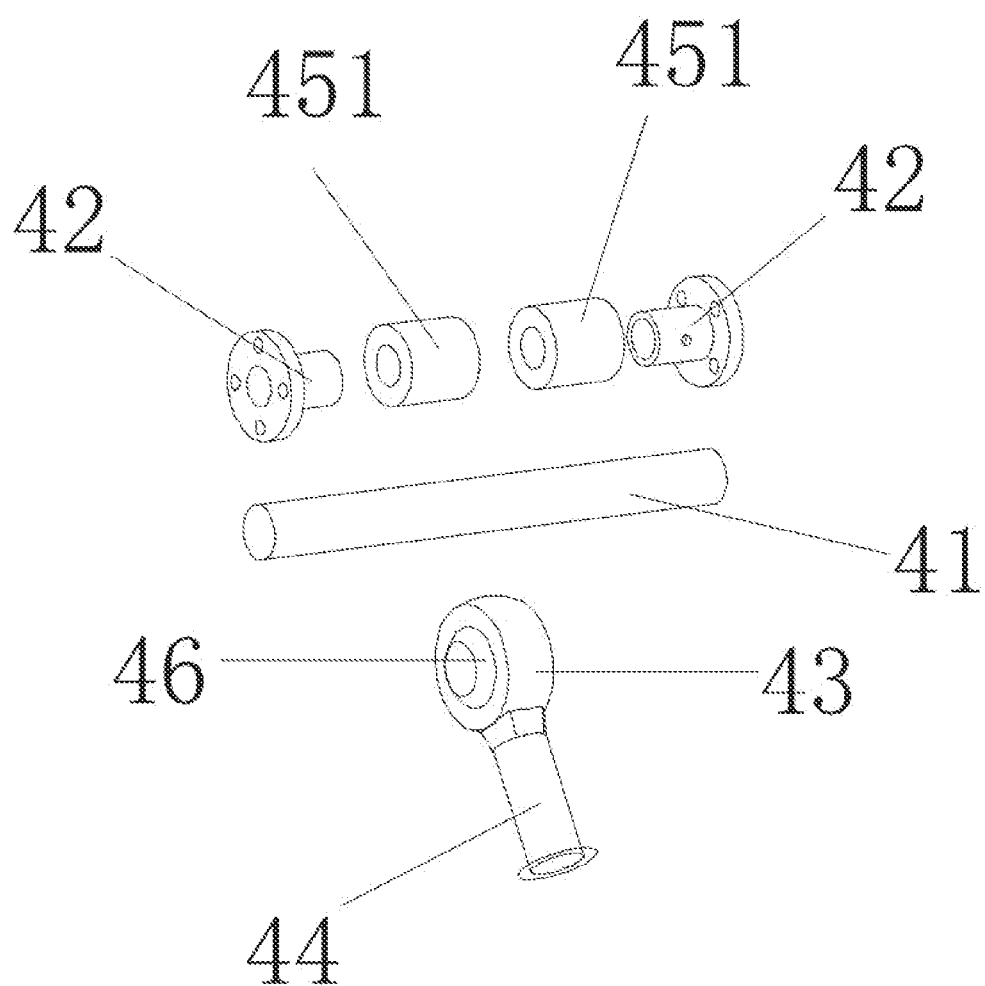
FIG. 9 is an exploded view of a first universal joint according to the present invention.
Figure 10:
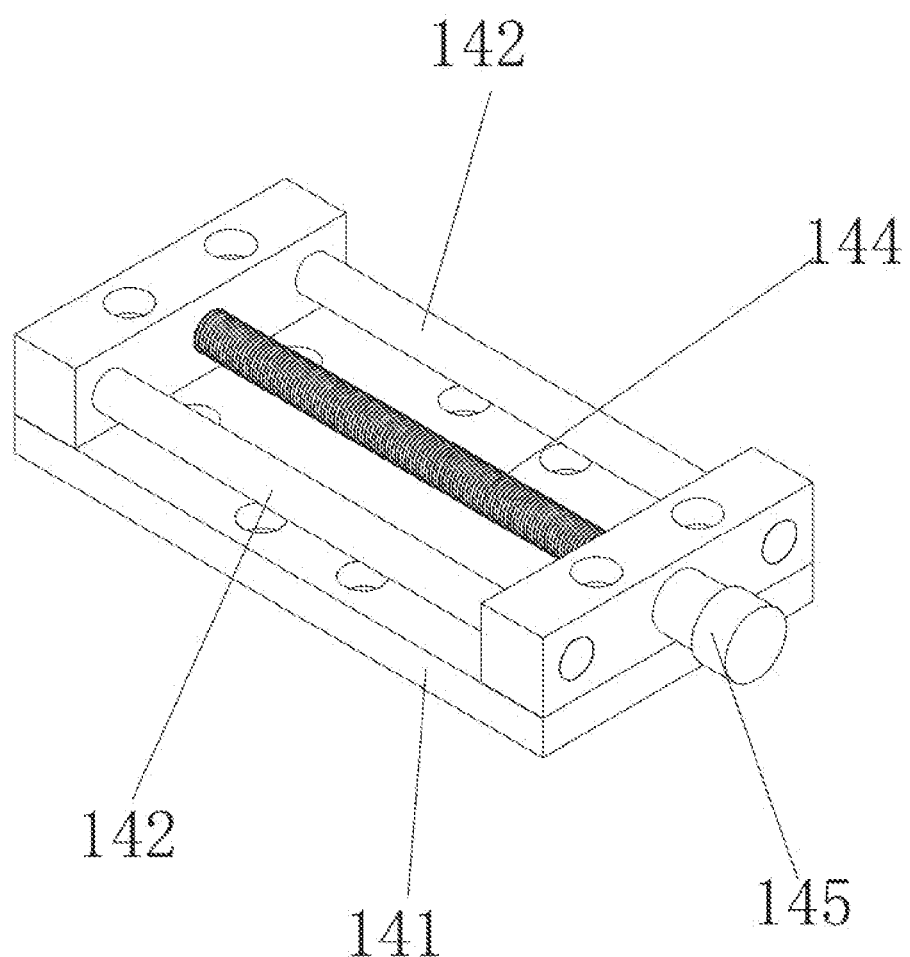
FIG. 10 is a stereoscopic view of a top ankle joint sliding table according to the present invention.
Figure 11:
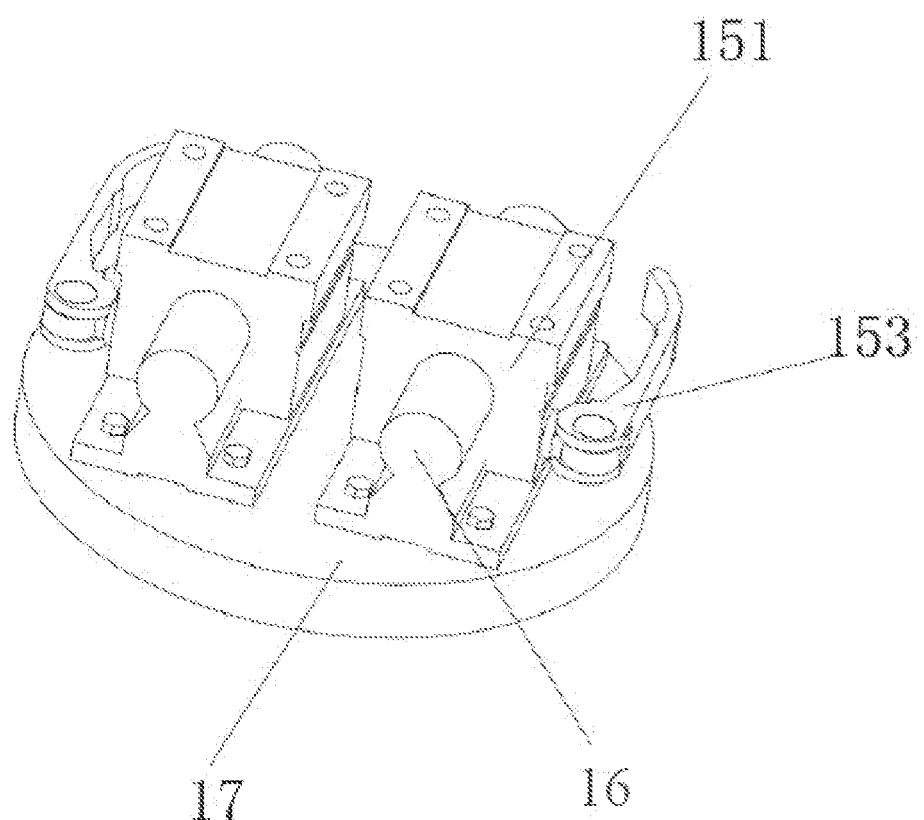
FIG. 11 is a stereoscopic view of a bottom ankle joint sliding table according to the present invention.

The fixed pulley blocks and the wire ropes are equal in number and corresponding. Each fixed pulley block includes a first fixed pulley 5a and a second fixed pulley 5b fixed on the sliding table 4, respectively. The first fixed pulley 5a is compressed and fixed by a bolt and a nut on the top. The bolt and the nut may be loosened to adjust an angle of the first fixed pulley. After the adjustment is in place, the first fixed pulley is tightened and fixed. As shown in FIG. 5, the second fixed pulleys 5b on both sides are inclined to the center, and are used to strand the wire ropes on both sides.

The ligament simulation band 10 and the patellar ligament simulation band 11 are made of an elastic material, such as rubber, and are respectively used to simulate a ligament. Both ends of the ligament simulation band are clamped and fixed by the upper and lower femoral ligament clamps respectively. The lower end of the patellar ligament simulation band is clamped by the patellar ligament clamp. The meniscus simulation block 91 matches the shape of the meniscus of the human body. The arc surface of the lower femur simulation block 8 corresponds to the shape of the lower femur of the human body. The arc surface at the lower end of the meniscus simulation block is supported on the meniscus simulation block 91. Since the upper end of the femoral shaft 7 and the lower end of the tibial shaft 12 are connected by a universal joint, when the device simulates the squat of the human body, the femoral shaft 7 and the tibial shaft 12 simulate the movement trail of the lower limb in a three-dimensional direction. This device simulates the main bone and soft tissue structure of the human lower limb, as well as the stress state of the main muscles and ligament tissues during squatting. Then the device tests the biomechanical properties of the knee joint of the human body during exercise, and acquires the biomechanical properties of the knee joint of the human body at various flexion angles, so as to comprehensively measure the forces and compound movement trails (medial/lateral rotation and adduction/abduction, etc.) of the human lower limb. Meanwhile, this device acquires basic data such as the forces on the joint and sole, provides a biomechanical data basis for the exercise, rehabilitation and surgical treatment of the lower limb and joint of the human body, and also provides effective bionic data for the production of lower limb prostheses.

As shown in FIG. 1, there are three wire ropes, which are used to simulate three main muscles of the lower limb. The second motors corresponding to the wire ropes rotate, so that a tension is transmitted through the three wire ropes, and a force is applied to the knee joint as a first input to simulate a muscle force. Through the rotation of the first motor, the lifting of the sliding table is controlled to simulate the squat of the human lower limb as a second input. The descending speed of the sliding table is a squatting speed. In the process of simulating the squat, the movement trail signal is acquired by the gyroscope, and the force signal is acquired by the strain gauge, so as to simulate the movement trail of the lower limb under a certain force. This device simulates the main bone and soft tissue structure of the human lower limb, as well as the stress state of the main muscles and ligament tissues during squatting. Then the device tests the biomechanical properties of the knee joint of the human body during exercise, and acquires the biomechanical properties of the knee joint of the human body at various flexion angles, so as to acquire the forces and compound movement trails of the human lower limb. This device provides a biomechanical data basis for the exercise, rehabilitation and surgical treatment of the lower limb and joint of the human body, and also provides effective bionic data for the production of lower limb prostheses. A final movement trail derived through detection is basically consistent with an actual situation, as follows:

1. Device Input

Figure 12:
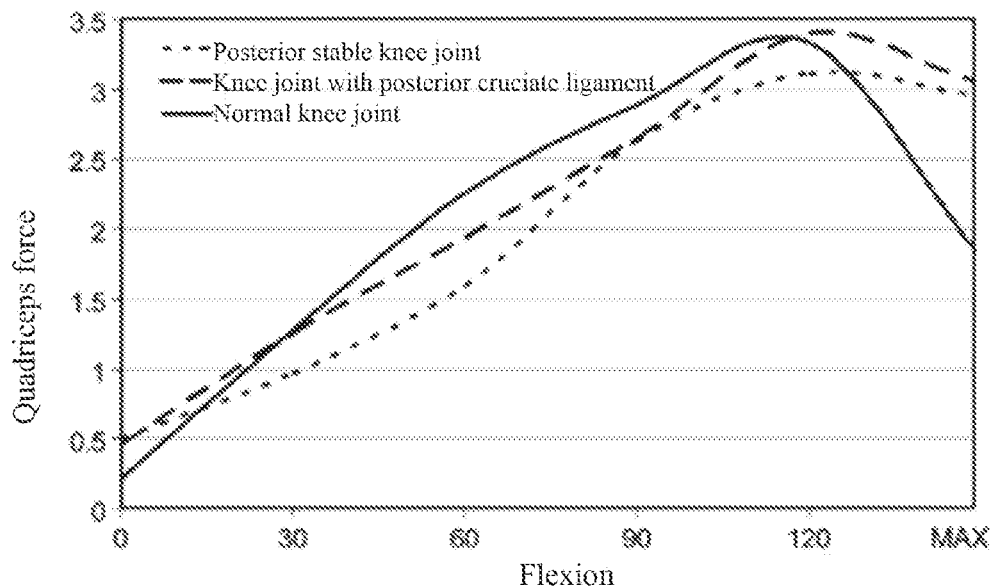
FIG. 12 shows a quadriceps force curve recorded by Sharma et al. in Literature [1].

This device performed force loading according to a normal knee joint curve of quadriceps femoris muscle published by Sharma et al. in 2008 (Literature [1]). The curves of three forces loaded are shown in FIG. 12.

[1] Sharma A, Leszko F, Komistek R D, et al. In vivo patellofemoral forces in high flexion total knee arthroplasty [J]. Journal of biomechanics, 2008, 41(3):642-648.

2. Device Output

The device acquired data through the gyroscope, and output the data of the knee joint in three dimensions, namely, flexion, medial/lateral rotation and adduction/abduction.

Figure 13:
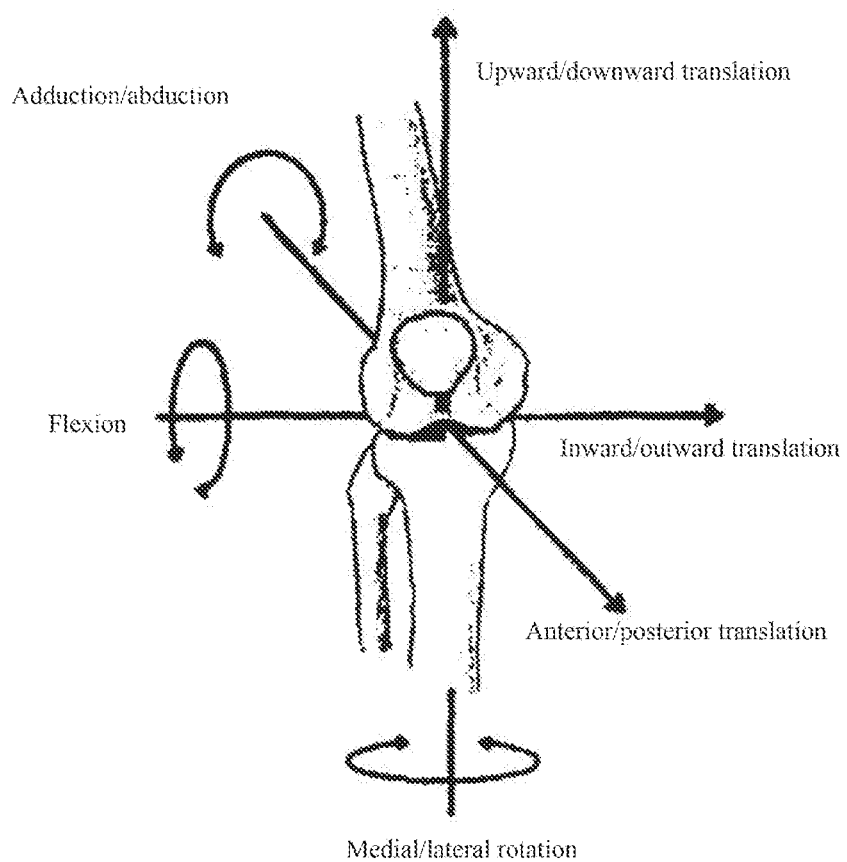
FIG. 13 is a schematic view of relative movements of a knee joint of a human body.

The three-dimensional movements of the knee joint include three translations and three rotations. As shown in FIG. 13, these three translations include upward/downward, anterior/posterior and inward/outward translations; these three rotations include medial/lateral rotation, adduction/abduction and flexion.

Figure 14:
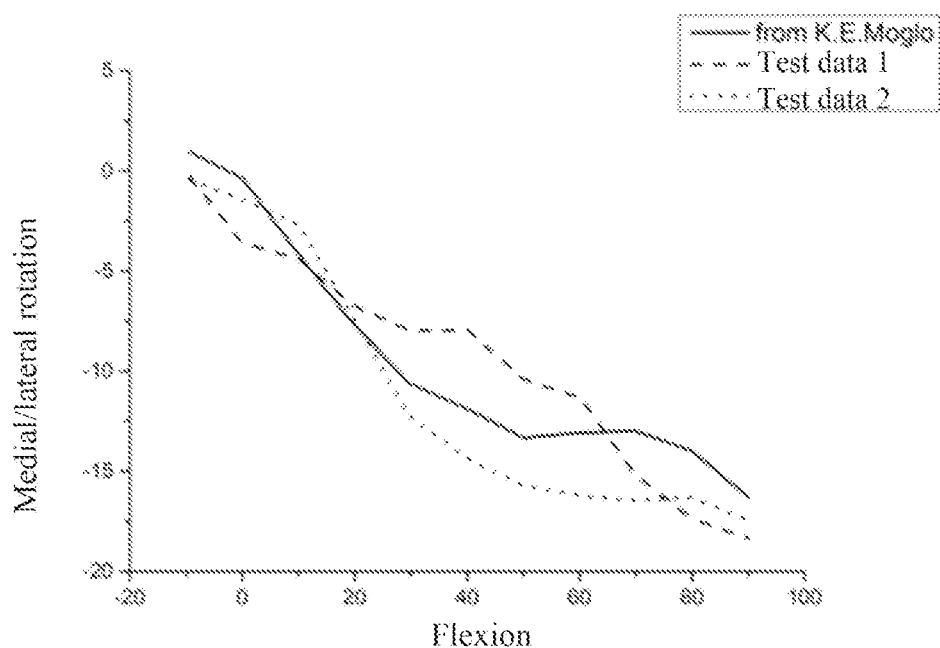
FIG. 14 shows a comparison of medial/lateral rotation of a femur of the knee joint relative to those of a tibia.
Figure 15:
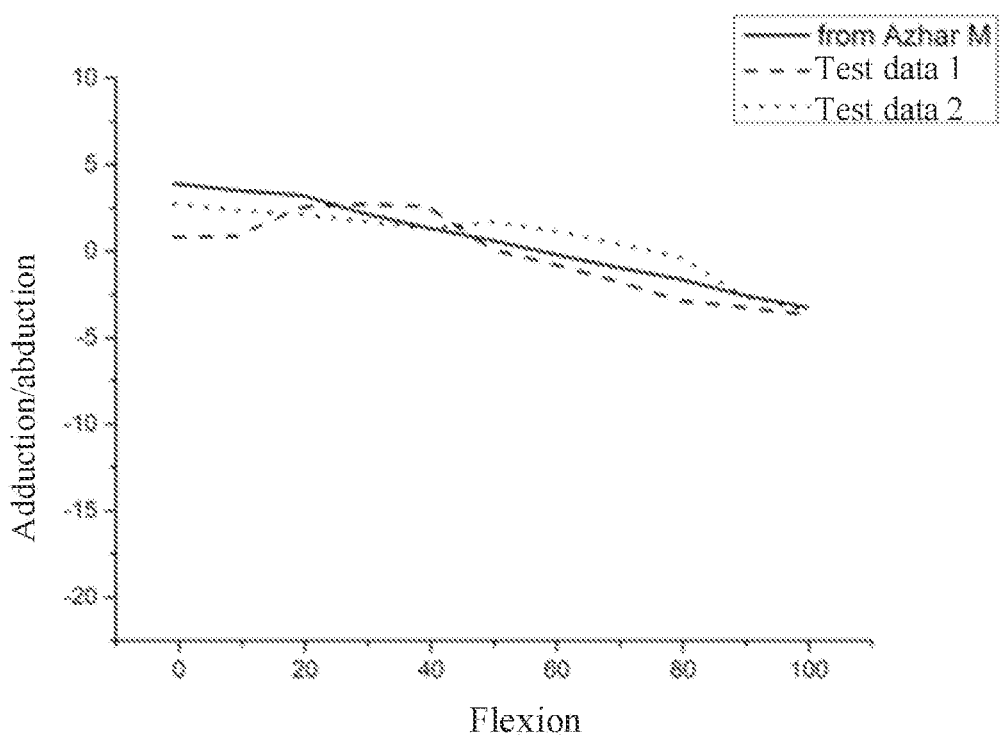
FIG. 15 shows a comparison of adduction/abduction of the femur of the knee joint relative to those of the tibia.

The test data derived by taking flexion as an abscissa and medial/lateral rotation and adduction/abduction as an ordinate were compared with the data of Sharma [1], as shown in FIGS. 14 and 15.

FIG. 14 shows a comparison of medial/lateral rotation of a femur of the knee joint relative to those of a tibia. Sharma et al. simulate the flexion by establishing a finite element model (FEM) and loading a relevant boundary condition. FIG. 14 shows that the data of Literature [1] and the test data of this device are basically consistent in the variation range of medial/lateral rotation. According to two sets of test data of this device, during knee squatting flexion, the femur is always in a state of lateral rotation relative to the tibia, which is similar to the results obtained by K. E. Moglo, et al. (Literature [2]). They believe that during knee flexion, the femur is always laterally rotated relative to the tibia; when the knee is flexed to about 50°, the femur is medially rotated relative to the tibia by a small amount, and then laterally rotated until the flexion ends. Their results are basically consistent with the test data of this device.

[2] K. E. Moglo, A. Shirazi-Adl, Cruciate coupling and screw-home mechanism in passive knee joint during extension-flexion. Journal of biomechanics, 2009, 38(5):1075-1083.

FIG. 15 shows a comparison of adduction/abduction of the femur of the knee joint relative to those of the tibia. In Literature [1], each component of the quadriceps femoris muscle is used to suspend a heavy object with a cable and a pulley, and a total load of 175 N is applied to the quadriceps femoris muscle to simulate flexion. The data of Literature [1] and the test data of this device are basically consistent in the variation range of adduction/abduction. According to the two sets of test data of this device, during knee squatting flexion, the femur is first adducted and then abducted relative to the tibia. This is similar to the results of Literature [3], and the movement mode is first adduction and then abduction. In Literature [3], the movement mode is to abduct at about 70° of flexion, which is basically consistent with the data of this device.

[3] Azhar M. Mexican, Andrew A. Amis, et al. Iliotibial band tension affects patellofemoral and tibiofemoral kinematics. Journal of biomechanics, 2009, 42(10):1539-1546.

3. Conclusion

The knee joint flexion, medial/lateral rotation and adduction/abduction measured by the present invention are compared with the data of these literatures. It shows that the movement modes of the knee joint are basically the same. The movement of the knee joint is continuous lateral rotation, first adduction and then abduction. The difference is that the maximum lateral rotation angle is about 5°, and the maximum adduction angle is about 3°, but both angles are within the error range of movement measurement. This proves the feasibility of the device of the present invention for movement measurement.

What is claimed is:

1. A squatting bionic device of a human lower-limb joint, comprising a support, wherein the support comprises a base and a vertical support plate, wherein the vertical support plate is vertically provided on one side of the base; the vertical support plate is provided thereon with a sliding table, wherein the sliding table is driven by a first motor to slide up and down in a height direction of the vertical support plate or to be fixed on the vertical support plate; a horizontal fixed shaft is fixed on the sliding table; the middle of the fixed shaft is connected with a femoral shaft through a first universal joint; a lower end of the femoral shaft is fixedly connected with a lower femur simulation block;

a plantar position adjustment mechanism is provided on the base; a tibial shaft is connected with the plantar position adjustment mechanism through a second universal joint; an upper end of the tibial shaft is connected with an upper tibia simulation block;

an upper end of the upper tibia simulation block is inserted with a meniscus connection block; an upper end of the meniscus connection block is provided with a meniscus clamping slot; a meniscus simulation block is compressed and fixed in the meniscus clamping slot on a top surface of the meniscus connection block;

a lower end of the lower femur simulation block is provided with a circular arc surface in a shape corresponding to a lower end of a human femur; the circular arc surface is supported on the meniscus simulation block; upper femoral ligament clamps are respectively fixed on two sides of the lower femur simulation block; lower femoral ligament clamps are respectively fixed on two sides of the upper tibia simulation block, wherein the lower femoral ligament clamps correspond to the upper femoral ligament clamps; a ligament simulation band is connected between the upper femoral ligament clamps and the lower femoral ligament clamps; a patellar ligament clamp is fixed on the front of the upper tibia simulation block; an upwardly extending patellar ligament simulation band is fixedly connected with the patellar ligament clamp;

a wire rope is wound around a rotation shaft of a second motor, wherein the second motor is fixed on the base; first end of the wire rope is fixed on the rotation shaft of the second motor, and a second end of the wire rope extends upwards, the second end of the wire rope passes around a fixed pulley block, wherein the fixed pulley block is fixed on the sliding table, and the second end of the wire rope is connected with an upper end of the patellar ligament simulation band.

2. The squatting bionic device according to claim 1, wherein a rail is provided in a vertical direction and is fixed on a side of the vertical support plate, wherein the side of the vertical support plate is adjacent to a center of the base; the rail is slidably provided with a sliding table fixing plate, wherein the sliding table fixing plate slides up and down in a length direction of the rail; the vertical support plate is fixed with the first motor above the rail; a lead screw is parallel to the length direction of the rail and is rotatably provided in front of the rail; a rotation shaft of the first motor faces vertically downward and a lower end of the rotation shaft of the first motor is fixedly connected with an upper end of the lead screw; the lead screw is screwed with a nut, wherein the nut is fixed with the sliding table fixing plate, to form a driving structure, wherein the driving structure makes the sliding table fixing plate slide up and down in the length direction of the rail; the sliding table is fixed on a side of the sliding table fixing plate, wherein the side of the sliding table fixing plate is away from the rail.

3. The squatting bionic device according to claim 2, wherein the first motor is fixed directly above the lead screw by a top motor fixing plate; the rotation shaft of the first motor passes through the motor fixing plate and is coaxially connected with the upper end of the lead screw through a coupling; a slider is fixed on a side of the sliding table fixing plate, wherein the side of the sliding table fixing plate is adjacent to the rail; the slider is slidably provided on the rail.

4. The squatting bionic device according to claim 2, wherein the squatting bionic device further comprises a controller, a tension sensor, a strain meter, a first gyroscope, a second gyroscope, a first strain gauge and a second strain gauge; the first strain gauge is provided between the top surface of the meniscus connection block and a bottom surface of the meniscus simulation block; the second strain gauge is provided between an upper surface of a bottom ankle joint sliding table and a lower surface of a top ankle joint sliding table; the tension sensor is provided on each wire rope; the first gyroscope is fixed on the femoral shaft; the second gyroscope is fixed on the tibial shaft; an output terminal of the controller is connected with the first motor and the second motor; an output terminal of the first strain gauge, an output terminal of the second strain gauge, an output terminal of the first gyroscope, an output terminal of the second gyroscope and an output terminal of the tension sensor are respectively connected with an input terminal of the controller.

5. The squatting bionic device according to claim 1, wherein the squatting bionic device further comprises a controller, a tension sensor, a strain meter, a first gyroscope, a second gyroscope, a first strain gauge and a second strain gauge; the first strain gauge is provided between the top surface of the meniscus connection block and a bottom surface of the meniscus simulation block; the second strain gauge is provided between an upper surface of a bottom ankle joint sliding table and a lower surface of a top ankle joint sliding table; the tension sensor is provided on each wire rope; the first gyroscope is fixed on the femoral shaft; the second gyroscope is fixed on the tibial shaft; an output terminal of the controller is connected with the first motor and the second motor; an output terminal of the first strain gauge, an output terminal of the second strain gauge, an output terminal of the first gyroscope, an output terminal of the second gyroscope and an output terminal of the tension sensor are respectively connected with an input terminal of the controller.

6. The squatting bionic device according to claim 5, wherein the controller is connected with a key, a display and a power supply, respectively.

7. The squatting bionic device according to claim 5, wherein the plantar position adjustment mechanism comprises a third motor fixed on the base; a rotation shaft of the third motor is vertically upward; the rotation shaft of the third motor is fixed with a turntable; the turntable is fixed with a first ankle joint guide rail; the first ankle joint guide rail is provided thereon with the bottom ankle joint sliding table, wherein the bottom ankle joint sliding table slides in a length direction of the first ankle joint guide rail or is fixed on the first ankle joint guide rail; the upper surface of the bottom ankle joint sliding table is connected with the top ankle joint sliding table; the second universal joint is provided on the top ankle joint sliding table; the third motor is connected with the controller.

8. The squatting bionic device according to claim 7, wherein a bottom of the bottom ankle joint sliding table is fixed with a first ankle joint guide slider, wherein the first ankle joint guide slider corresponds to the first ankle joint guide rail; the first ankle joint guide slider is slidably placed on the first ankle joint guide rail;

the top ankle joint sliding table comprises a sliding table base; the sliding table base is provided with a second ankle joint guide rail and a guide screw, wherein the guide screw is parallel to the second ankle joint guide rail; the second ankle joint guide rail is slidably connected with a second ankle joint guide slider, wherein the second ankle joint guide slider slides back and forth in a length direction of the second ankle joint guide rail; the second ankle joint guide slider is threadedly connected with the guide screw; a position adjustment knob is fixed on the guide screw, wherein the guide screw extends from one side of the sliding table base; the second universal joint is connected with the second ankle joint guide slider.

9. The squatting bionic device according to claim 1, wherein the fixed shaft is fixed between two side walls of the sliding table through shaft seats at two ends; opposite clamping sleeves are fixed and sleeved on two sides of the fixed shaft, respectively; the first universal joint is provided between the two clamping sleeves; the first universal joint comprises a spherical support fixed between the two clamping sleeves; an upper end of the femoral shaft is fixedly connected with a femoral joint extension connector, wherein the femoral joint extension connector is coaxial with the femoral shaft; a femoral joint bearing sleeve is fixed at an upper end of the femoral joint extension connector; the femoral joint bearing sleeve is movably sleeved on the spherical support to form a universal connection structure.

10. The squatting bionic device according to claim 1, wherein a wire rope stranding guide sleeve is fixed on the femoral shaft; three second motors are provided; the rotation shaft of each of the three second motors is wound with the wire rope; the three wire ropes pass around the fixed pulley block, the three wire ropes pass through the wire rope stranding guide sleeve, and the three wire ropes are connected with the upper end of the patellar ligament simulation band.

* * * * *